(12) United States Patent
Richardson et al.

(10) Patent No.: US 10,980,660 B2
(45) Date of Patent: Apr. 20, 2021

(54) QUICK RELEASE RESTRAINT RING

(71) Applicants: Jed C. Richardson, Batavia, IL (US);
Abdullah Shahzad, Aurora, IL (US)

(72) Inventors: Jed C. Richardson, Batavia, IL (US);
Abdullah Shahzad, Aurora, IL (US)

(73) Assignee: The Norix Group, Inc., West Chicago, IL (US)

( * ) Notice: Subject to any disclaimer, the term of this patent is extended or adjusted under 35 U.S.C. 154(b) by 0 days.

(21) Appl. No.: 15/871,057

(22) Filed: Jan. 14, 2018

(65) Prior Publication Data

US 2019/0374371 A1 Dec. 12, 2019

(51) Int. Cl.
*A61F 5/37* (2006.01)
*E05B 73/00* (2006.01)

(52) U.S. Cl.
CPC .......... *A61F 5/3769* (2013.01); *A61F 5/3792* (2013.01); *E05B 73/00* (2013.01); *Y10T 403/592* (2015.01)

(58) Field of Classification Search
CPC ................ A61F 5/3769; A61F 5/3792; Y10T 403/1683; Y10T 403/592; E05B 73/00
USPC ..................................... 403/DIG. 4
See application file for complete search history.

(56) References Cited

U.S. PATENT DOCUMENTS

| | | | | |
|---|---|---|---|---|
| 2,480,662 A * | 8/1949 | McKinzie | ............... | F41C 23/02 42/85 |
| 4,305,614 A * | 12/1981 | Holka | ..................... | B60J 5/101 16/252 |
| 4,998,308 A * | 3/1991 | Farago | .................. | A61F 5/3776 128/869 |
| 6,929,438 B1 * | 8/2005 | Foster | ..................... | B60P 7/083 410/100 |
| 7,476,069 B2 * | 1/2009 | Facey | ..................... | B60P 7/083 410/100 |
| 7,562,481 B2 * | 7/2009 | Esch | ....................... | F41C 23/02 224/150 |
| 7,654,027 B1 * | 2/2010 | Grover | .................... | F41C 23/02 42/85 |
| 7,717,269 B2 * | 5/2010 | Bacho | ....................... | B07B 1/46 209/399 |
| 8,500,358 B1 * | 8/2013 | Cassidy | ............... | A63B 21/156 403/322.2 |
| 8,516,732 B2 * | 8/2013 | Burnsed, Jr. | .......... | F41C 33/002 42/85 |
| 8,955,866 B2 * | 2/2015 | Bowe | ....................... | B60D 1/06 280/511 |
| 9,248,537 B2 * | 2/2016 | O'Neill | ................ | F16B 21/165 |
| 10,550,609 B2 * | 2/2020 | Llewellyn | ............... | E05B 73/00 |
| 10,731,945 B2 * | 8/2020 | Tower | .................... | F41C 23/02 |
| 2018/0087867 A1 * | 3/2018 | Tower | ................... | F16B 21/165 |

* cited by examiner

*Primary Examiner* — Matthew R McMahon
(74) *Attorney, Agent, or Firm* — James D Palmatier; Applied Patent Services, PC (57) ABSTRACT

The present invention comprises a kit of a restraint ring, a base and a quick release, tamper resistant fastener. The base is adapted to attach to a fixture. The fixture may be a bed, chair, floor or wall. The base may be attached using tamper resistant fasteners. The base may be permanently attached or may be removably attached. The base is adapted to releasably receive the quick release fastener thereby attaching the restraint ring to the base.

10 Claims, 11 Drawing Sheets

QUICK RELEASE RESTRAINT RING

FIELD OF THE INVENTION

The present invention relates generally to restraint rings used in facilities to attach individuals to an object to restrict their movement.

BACKGROUND OF THE INVENTION

Restraint rings have been used to restrain people for their own safety and for the safety of those around them. Restraint rings comprise a ring or fixture attached to a chair, bed or the floor. The ring is adapted to receive a strap, rope or chain that is looped through the ring and attaches to the subject to another ring to restrict movement. A restraint ring may be used with hand cuffs having one cuff on the subjects arm or leg and the other cuff attached to the restraint ring.

Restraint rings may also be used with straps to strap a subject to a bed or chair by connecting a first end of the strap to a first restraint ring, extending the strap over the subject having the subject between the strap and the bed and attaching a second end of the strap to a second restraint ring whereby the strap bears against the subject to restrain movement.

Restraint rings must be secured to be effective. The restraint ring should be anchored to a floor, wall or a piece of furniture that is anchored or ballasted to restrain movement. The restraint ring may be securely attached to a sturdy piece of furniture for restraining the subject to the furniture such as a bed or chair.

Restraint rings may be used in incarceration type situations such as jails or police holding areas as well as health care facilities to restrain patients. The sight of a restraint ring on a piece of furniture may be intimidating in a health care facility thus causing stress in the patient. Therefore, a quick release restraint ring is needed that can be easily and quickly attached and removed to a piece of furniture.

BRIEF SUMMARY OF THE PRESENT INVENTION

The present invention comprises a kit of a restraint ring, a base and a quick release, tamper resistant fastener. The base is adapted to attach to a fixture. The fixture may be a bed, chair, floor or wall. The base may be attached using tamper resistant fasteners. The base may be permanently attached or may be removably attached. The base is adapted to releasably receive the quick release fastener thereby attaching the restraint ring to the base. The restraint ring may be made of metal or plastic or a restraint material.

The quick release fastener engages the base and bears against the restraint ring to provide secure anchoring of the restraint ring. Actuating the quick release fastener disengages the base and allows the restraint ring to be removed.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DETAILED DESCRIPTION OF THE INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention. It is to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting. It should be appreciated that the invention can be used for any suitable.

Referring to FIGS. 1-5 the invention comprises a base 10 having a mounting surface 12 and a restraint ring 14 attached to the mounting surface 12. The restraint ring 14 has an open loop portion 16 and a ring base 18. Mounting hole 32 extends through base 10. Quick release fastener 24 extends through ring base 18 in quick release hole 30. Quick release fastener 24 engages base 10 to secure restraint ring 14 to base 10. Stabilizers 20 on mounting surface 12 to urge restraint ring 14 to maintain a predetermined orientation with respect to base 10. It is preferable that open loop portion 16 is spaced from base 10. Quick release fastener 24 comprises head 40 bearing against restraint ring 14 to attach restraint ring 14 to base 10 having ring shaft extending through ring 14 and into base 10 with quick release shaft extending on quick release hole 30 to dispose locking mechanism 46 in position to bear against locking shoulder 58.

Referring to FIGS. 6-10, base 10 has a first side 26 and second side 28. Quick release hole 30 opens to first side 26 having quick release shaft 44 removably attached therein. Restraint ring 14 comprises strap opening 22 on open loop portion 16. Secure hole 32 extends through base 10 generally perpendicular to quick release hole 30. Quick release fastener 24 may have a release mechanism 25 adapted to securely release and prevent unauthorized removal of restraint ring 14.

Figures 1, 2:
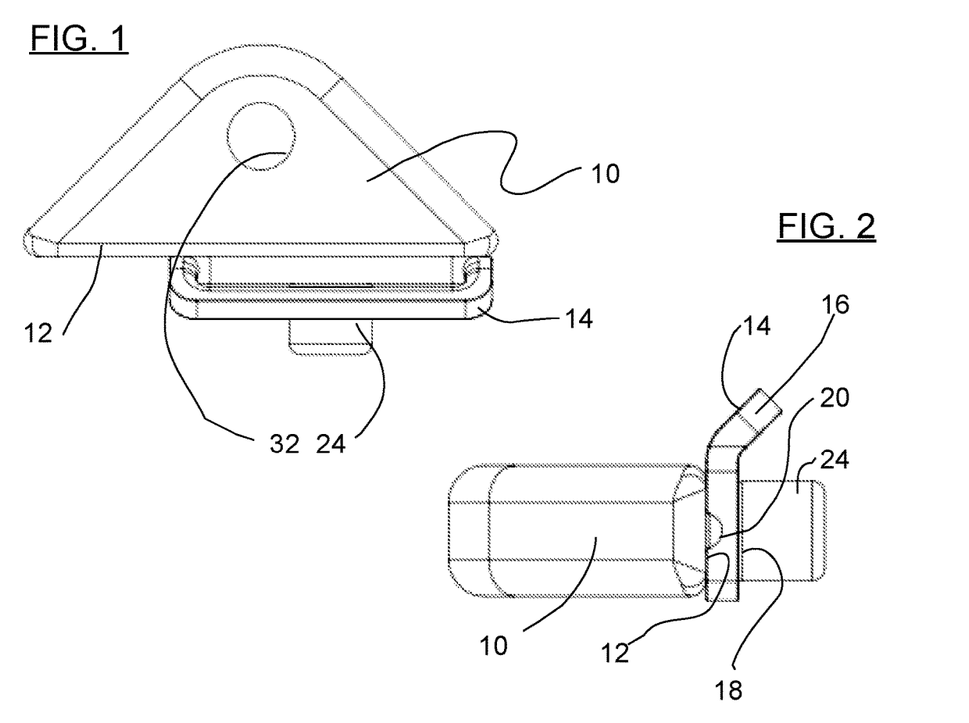
FIG. 1 is a top plan view of a first embodiment of the present invention.
FIG. 2 is a right side elevation view of the first embodiment of the present invention of FIG. 1
Figure 3:
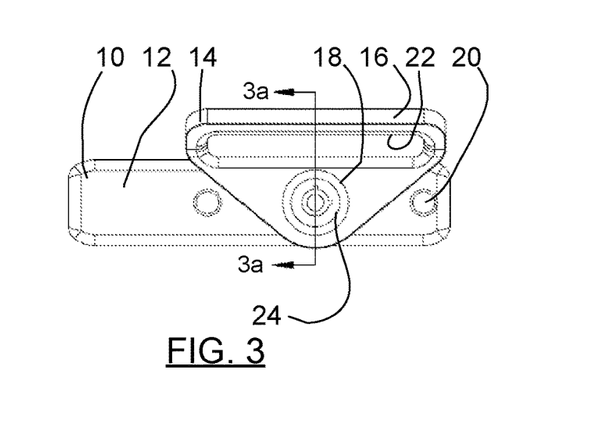
FIG. 3 is a front elevation view of the first embodiment of the present invention of FIG. 1.
Figure 3A:
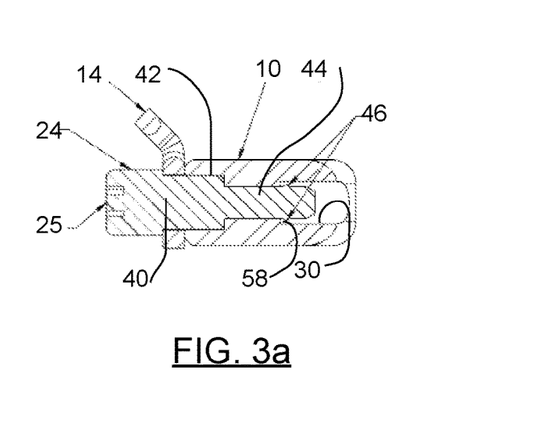
FIG. 3a is a section view of the first embodiment taken at approximately 3a-3a of FIG. 3.
Figure 4:
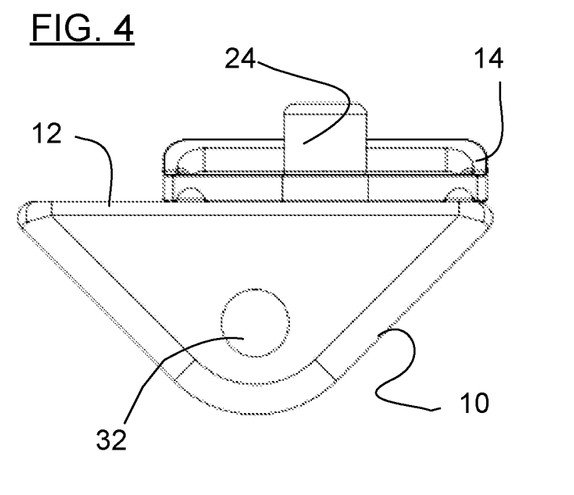
FIG. 4 is a bottom plan view of the first embodiment of the present invention of FIG. 1.
Figure 5:
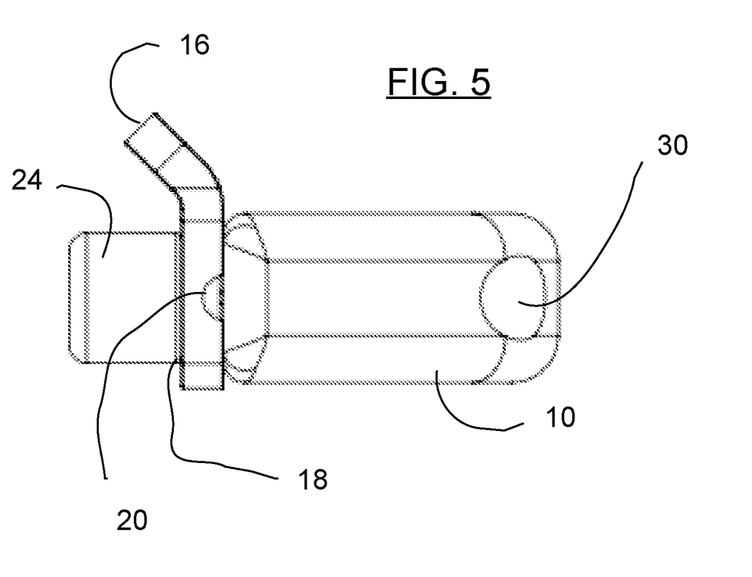
FIG. 5 is a left plan view of the first embodiment of the present invention of FIG. 1.
Figure 6:
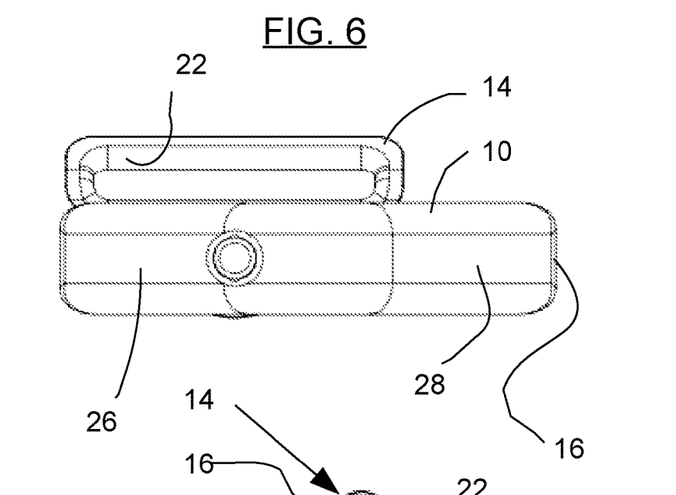
FIG. 6 is a back elevation view of the first embodiment of the present invention of FIG. 1.
Figures 7, 8:
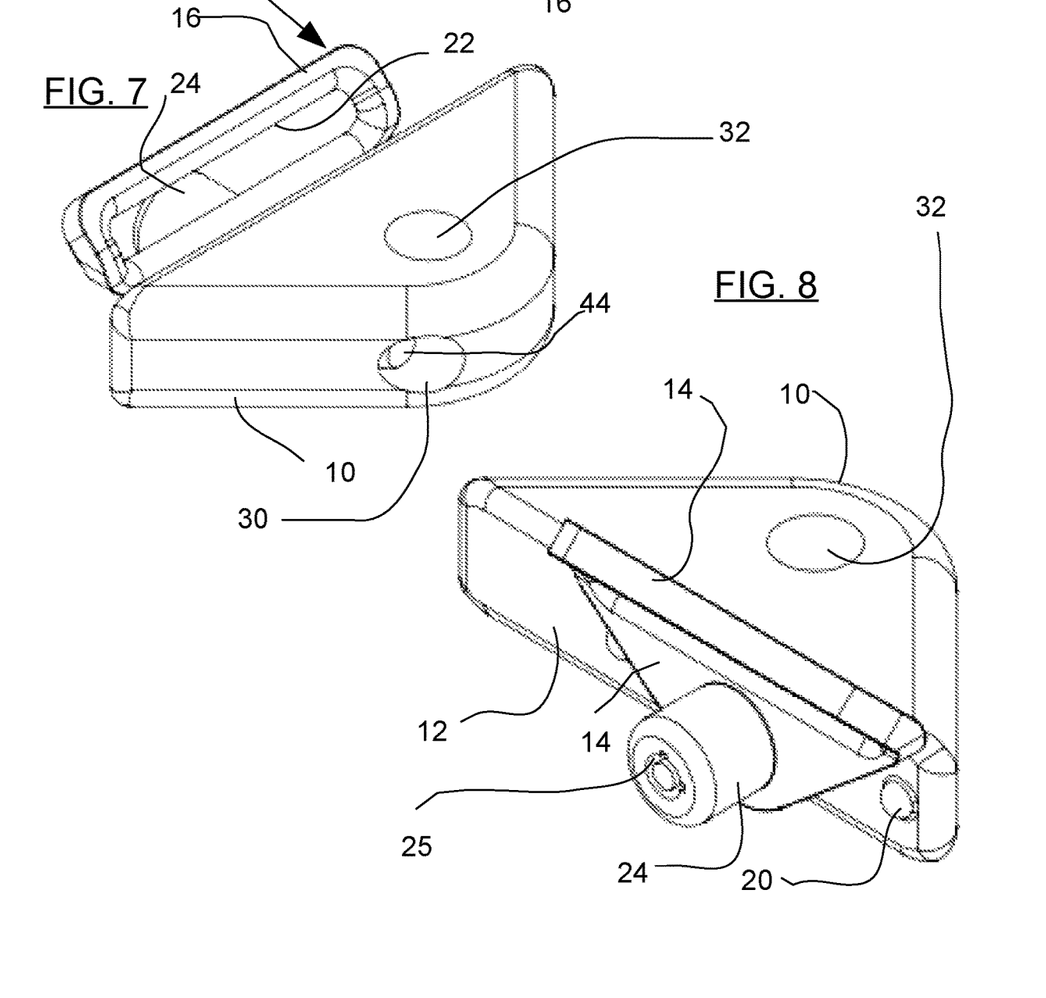
FIG. 7 is a top back perspective view of the first embodiment of the present invention of FIG. 1
FIG. 8. is a top front perspective view of the first embodiment of the present invention of FIG. 1.
Figure 9:
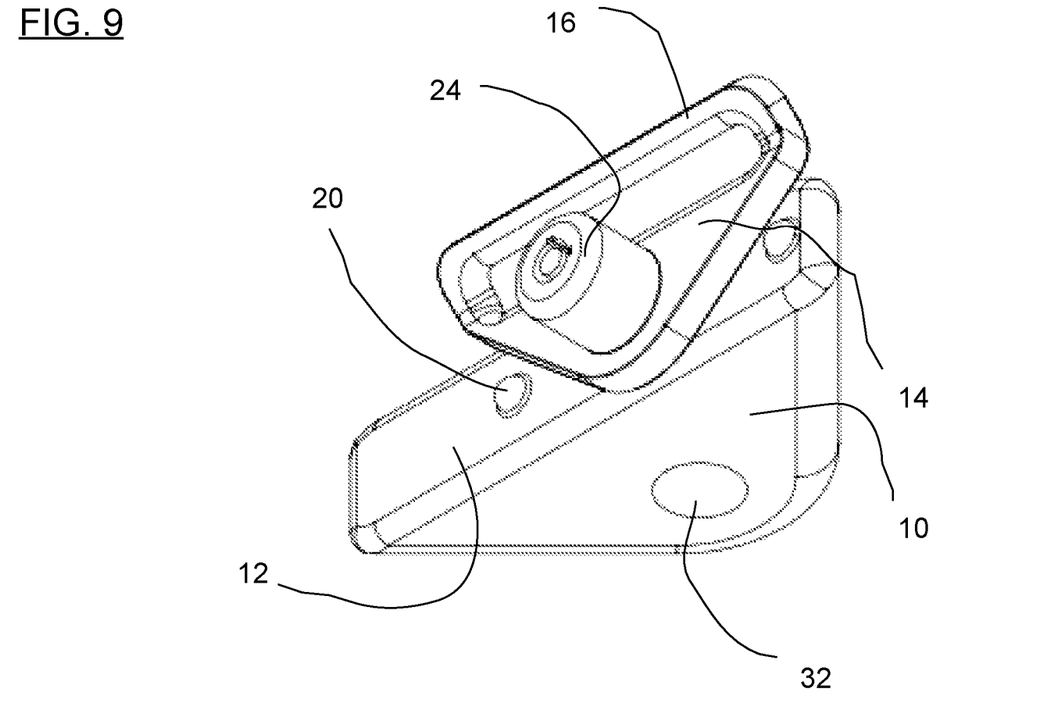
FIG. 9 is a bottom front perspective view of the first embodiment of the present invention of FIG. 1.
Figure 10:
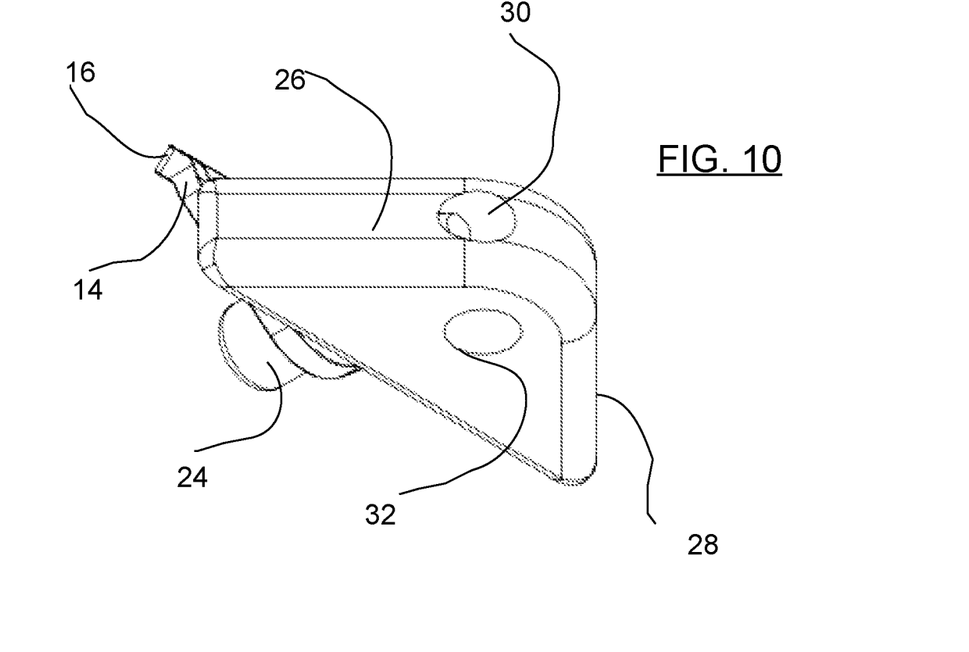
FIG. 10 is a bottom perspective view of the first embodiment of the present invention of FIG. 1.
Figure 11:
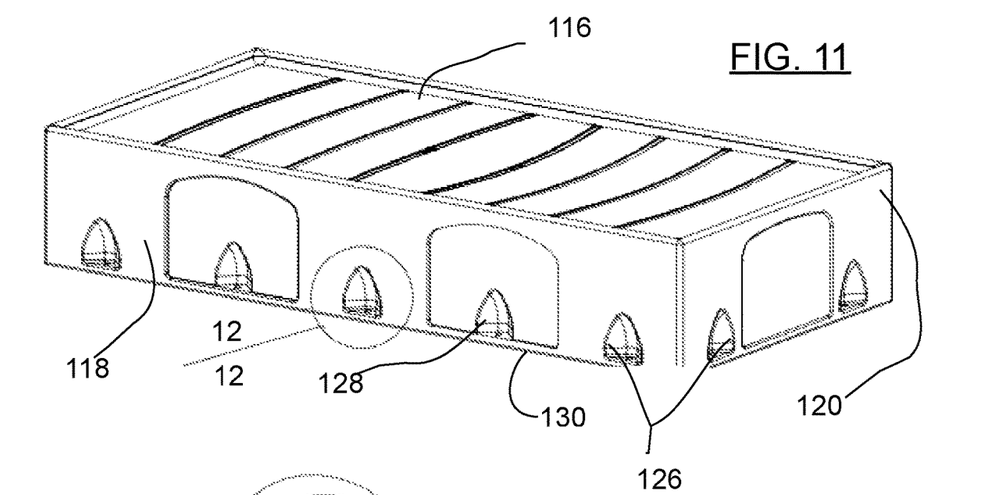
FIG. 11 is a perspective view of a bed adapted to attach to the first embodiment of the present invention of FIG. 1.
Figure 12:
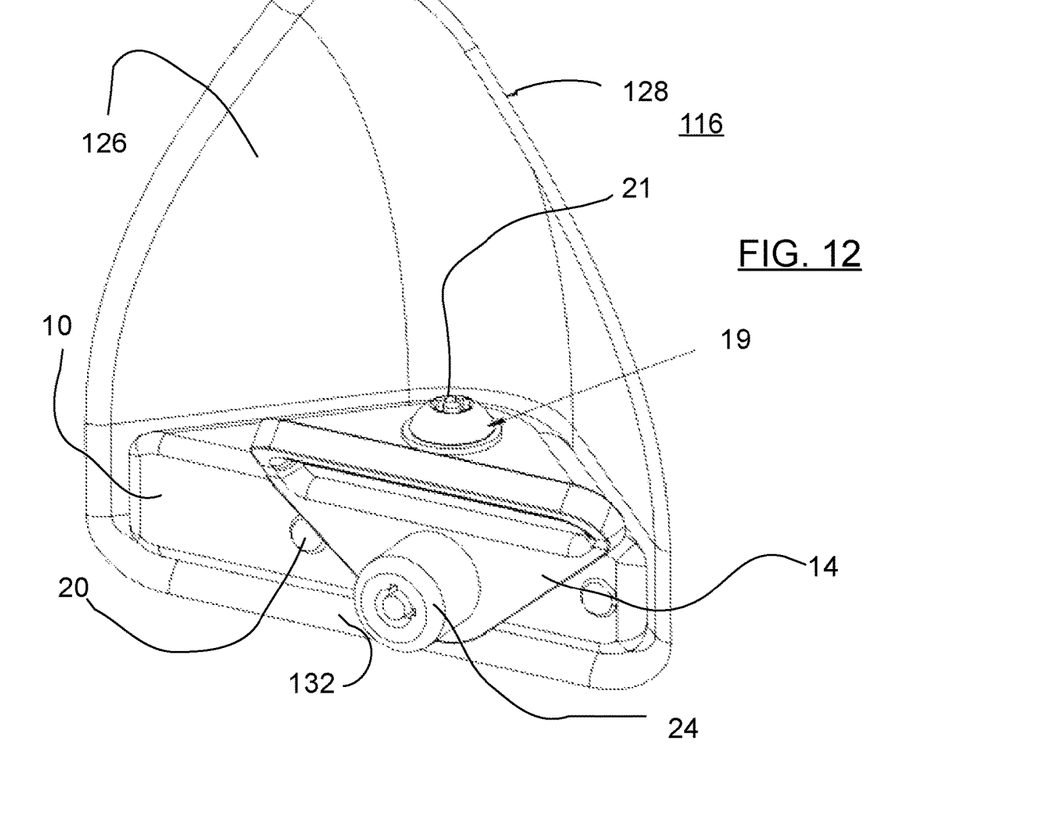
FIG. 12 is a section view of the first embodiment of the present invention of FIG. 1 attached to the bed of FIG. 11.

Referring to FIG. 11-12, bed 116 may have a side wall 118 having fastener coves 128 molded therein adjacent the bed bottom 130. Cove 128 comprises a side wall 126 and bottom wall 132. Anchor fastener 19 extends through base 10 to engage bottom wall 132 to removably attach base 10 to bed 116. Anchor fastener 19 may be a threaded fastener having a tamper resistant head 21. Anchor fastener may alternatively attach base 10 to floor or wall.

Figure 13:
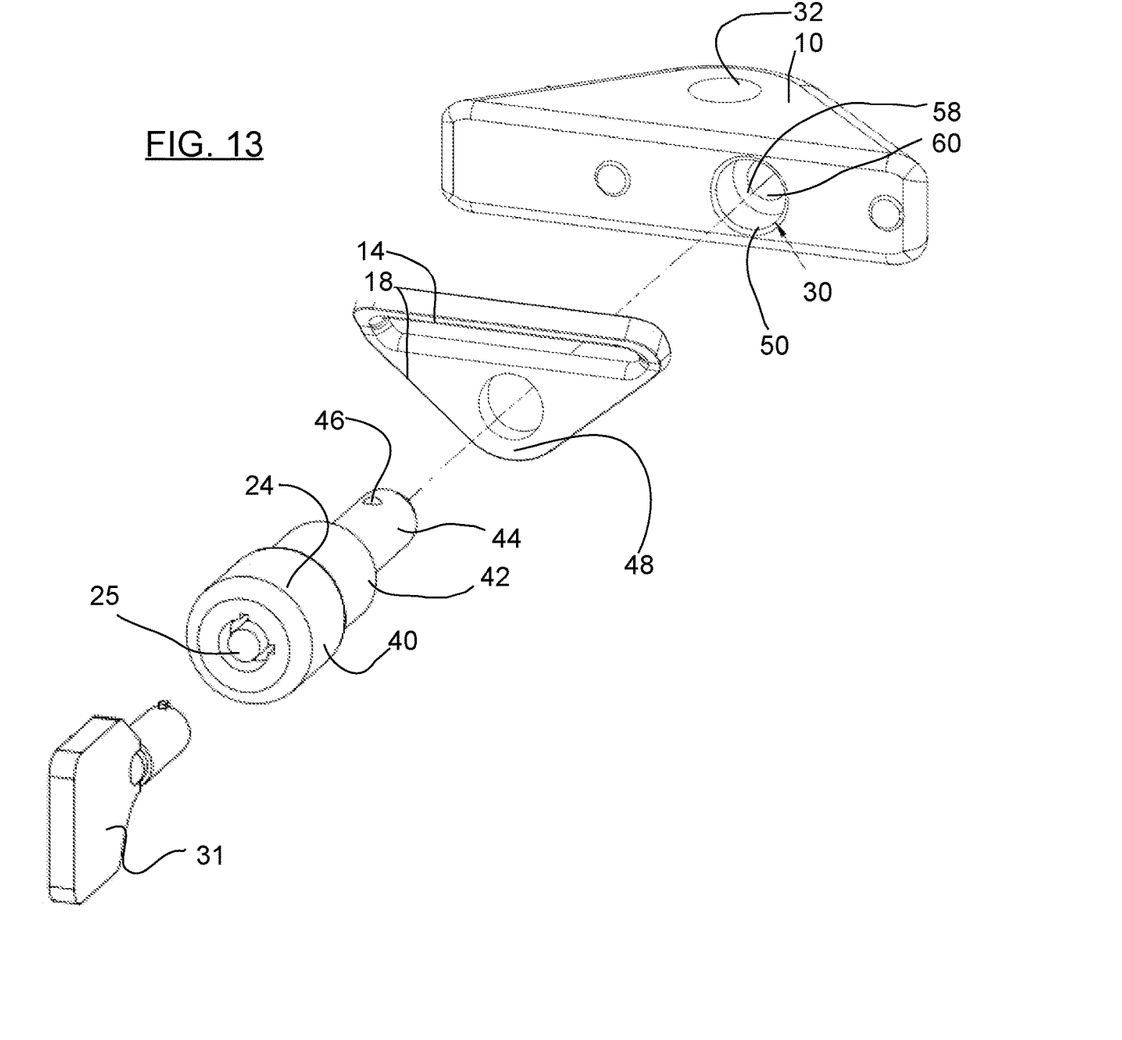
FIG. 13 is an exploded view of the first embodiment of the present invention.

Referring to FIG. 13. Quick release fastener 24, may have locking head 40 with release mechanism 25. Release mechanism 25 may be operated by actuator 31 adapted to release quick release fastener 24 from base 10. Release mechanism 25 may be a key, a magnetic actuator, a bio-metric scanner, a remote control release, a combination lock or other actuator device. Quick release fastener 24 may comprise a head 40 having a ring shaft 42 extending therefrom. A base shaft 44 may extend from ring shaft 42. Base shaft 44 may have locking mechanism 46 contained therein. Locking mechanism 46 may have retractable fixtures extending perpendicular to base shaft 44. Locking mechanism 46 may be actuated by release mechanism 25.

Continuing to refer to FIG. 13, quick release hole 30 may comprise ring opening 50 and locking shoulder 58 and shaft portion 60. Restraint ring 14 may have a restraint hole 48 extending there-through. When assembled, ring shaft 42 is adapted to extend into shaft portion. Locking mechanism 46 releasably engages locking shoulder 58. ring shaft extends through restraint hole 48 and is in ring opening 50. Release mechanism 25 actuates the locking mechanism 46 into a non-locking configuration whereby quick release fastener is extended through restraint hole 48 and into base 10 at quick release hole 30. Base shaft 44 in shaft portion 60 is adapted to hold locking mechanism adjacent locking shoulder 58. Release mechanism 25 may be disengaged to extend locking mechanism 46 adapted to bear against locking shoulder 58. Head 40 bears against ring base 18 thereby removably securing restraint ring 14 to base 10.

Figure 14:
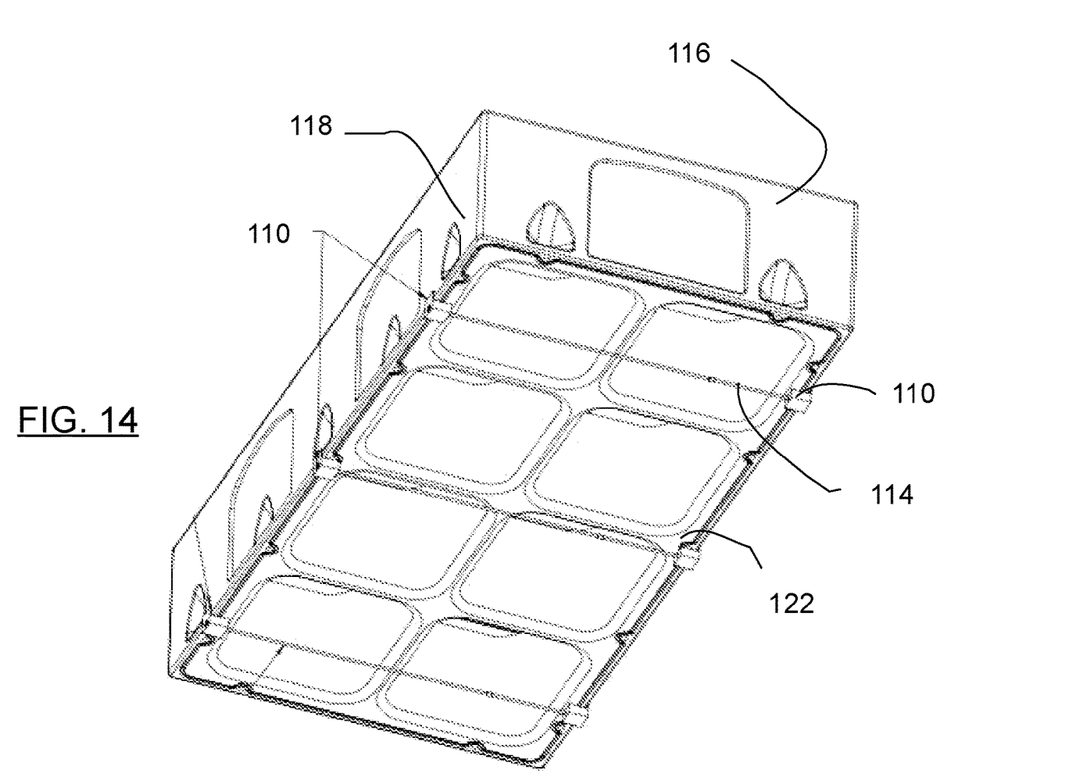
FIG. 14 is a bottom perspective view of a second embodiment of the present invention attached to a bed.
Figure 15:
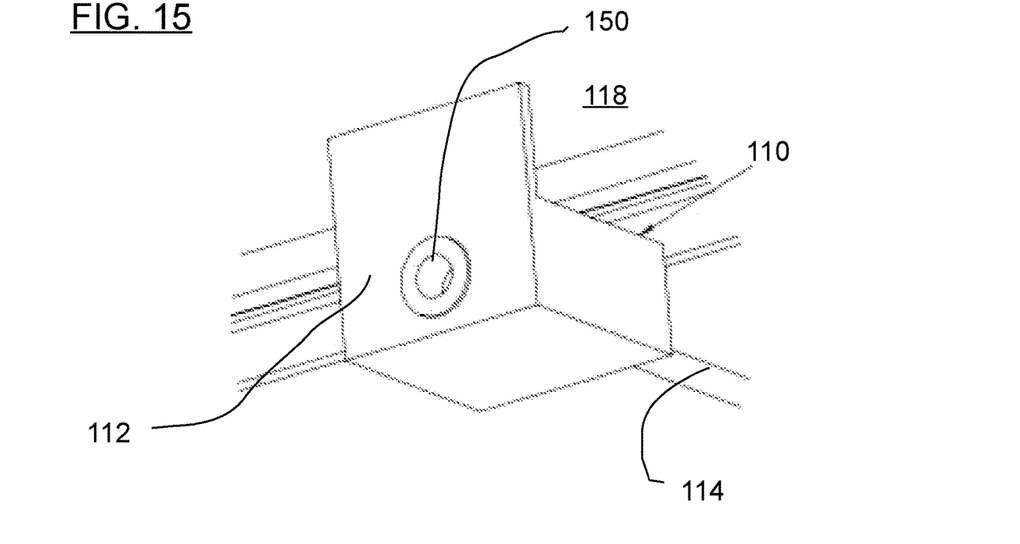
FIG. 15 is a perspective view of the second embodiment of the present invention.

Referring to FIGS. 14 and 15, base 110 may be attached to the bed by rod 114 extended under bed 116. Rod 114 may be attached to first and second base 110. First and second base 110 bear against sidewalls 118 to dispose ring opening 150 adapted to receive quick release fastener 24. base 110 may have flange 112 bearing against bed 116.

Figure 16:
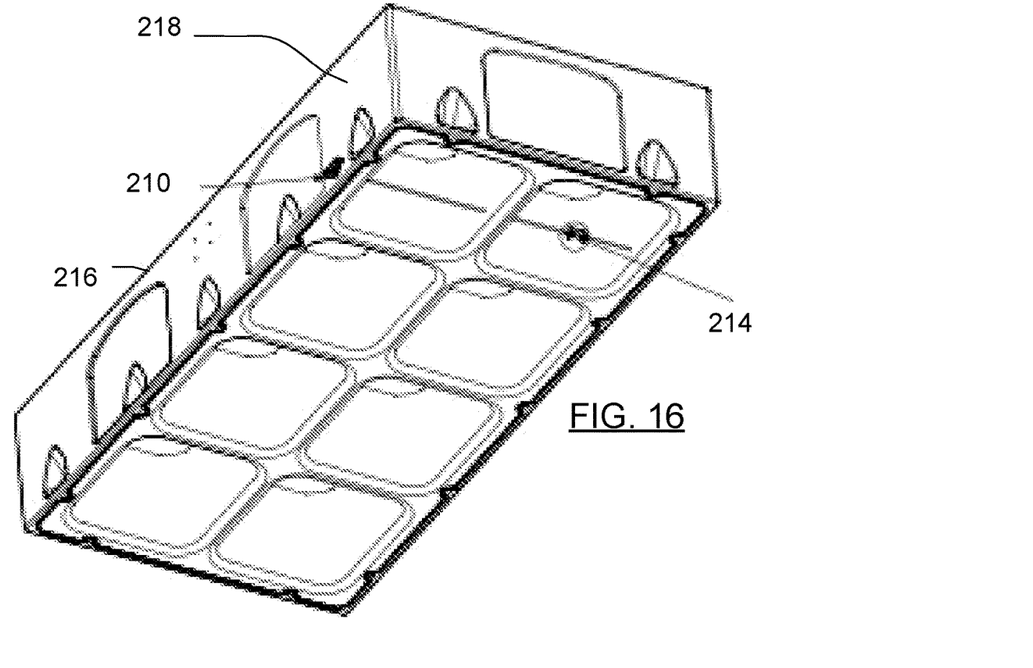
FIG. 16 is a perspective view of a third embodiment of the present invention.
Figure 17:
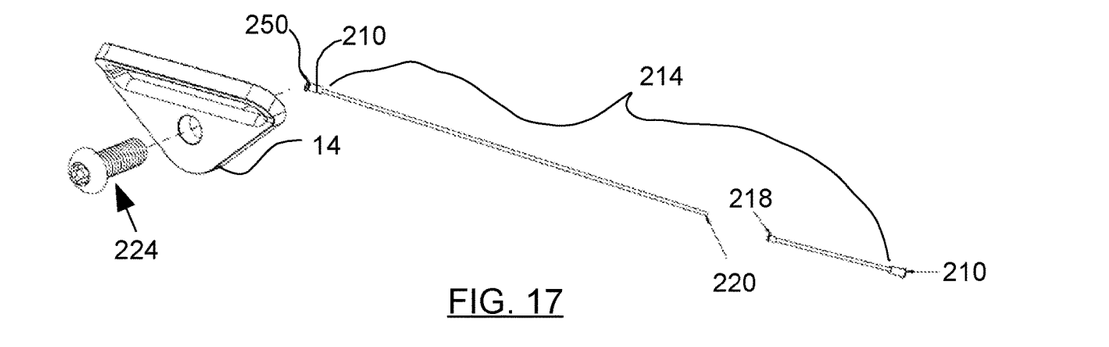
FIG. 17 is an exploded view of the third embodiment of the present invention.

Referring to FIGS. 16 and 17, base 210 may comprise ring opening 250 on the end of shaft 214. Shaft 214 may be pierced through bed 216. Ring opening 250 may be adapted to removably receive quick release fastener 224. Quick release fastener 224 may releasably connect restraint ring 14 to bed 216. Threaded coupling 218, 220 may be used to adapt shaft 214 to dispose base 210 on outside wall 218 of bed 216.

Figures 18, 19, 20:
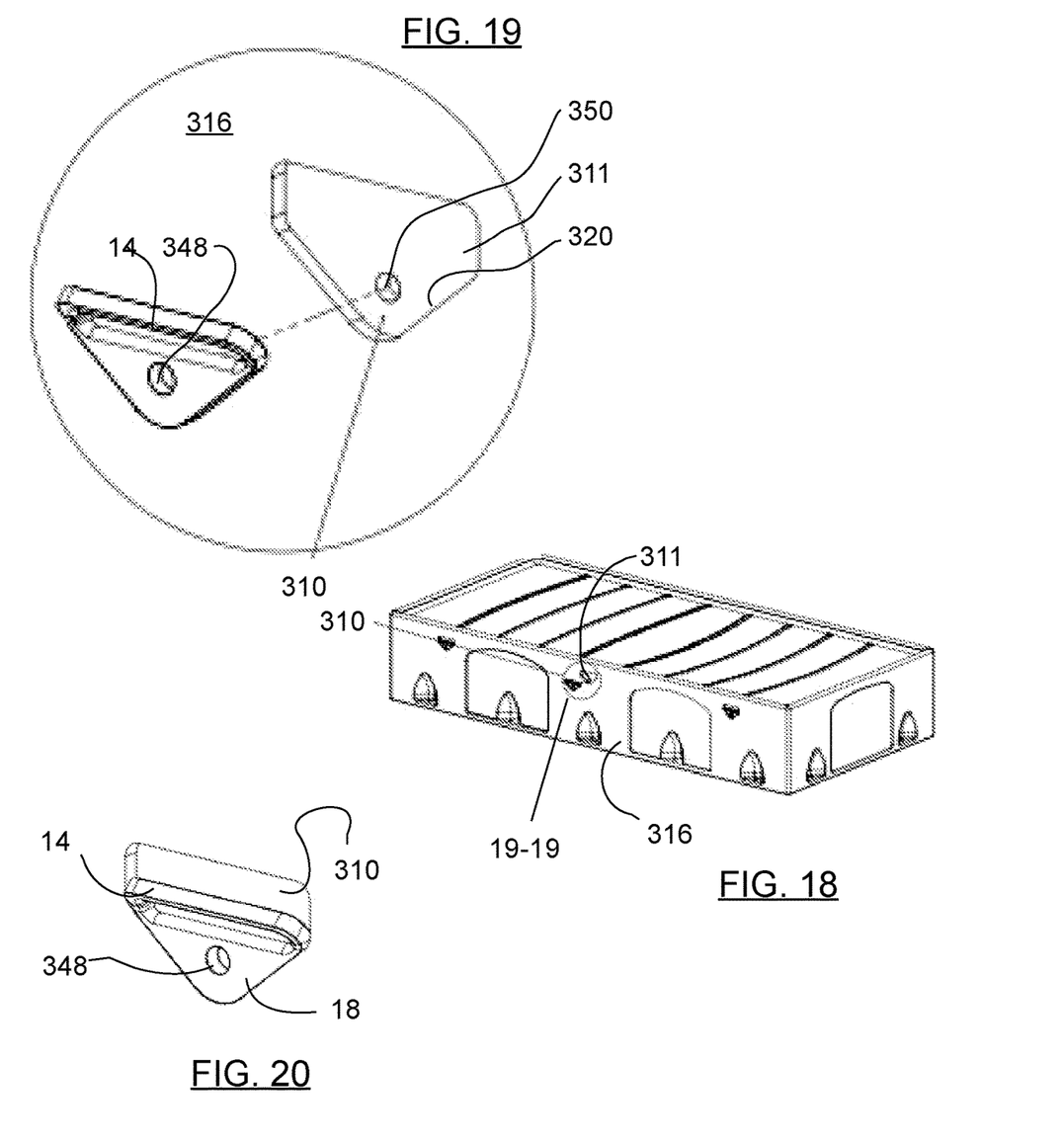
FIG. 18 is a perspective exploded view of the fourth embodiment of the present invention.
FIG. 19 is an exploded section view of the fourth embodiment of the present invention taken at approximately 19-19 of FIG. 18.
FIG. 20 is a section view of the fourth embodiment of the present invention taken at approximately 19-19 of FIG. 18

Referring to FIGS. 18-20, base 310 may comprise a pocket 311 formed on a molded bed 316. Pocket 311 may further comprise ring opening 350 and stabilizer edge 320 adapted to engage restraint ring 14 to hold restraint ring 14 in a predetermined orientation. Restraint hole 348 is disposed to align with ring opening 350.

Figures 21, 22, 23:
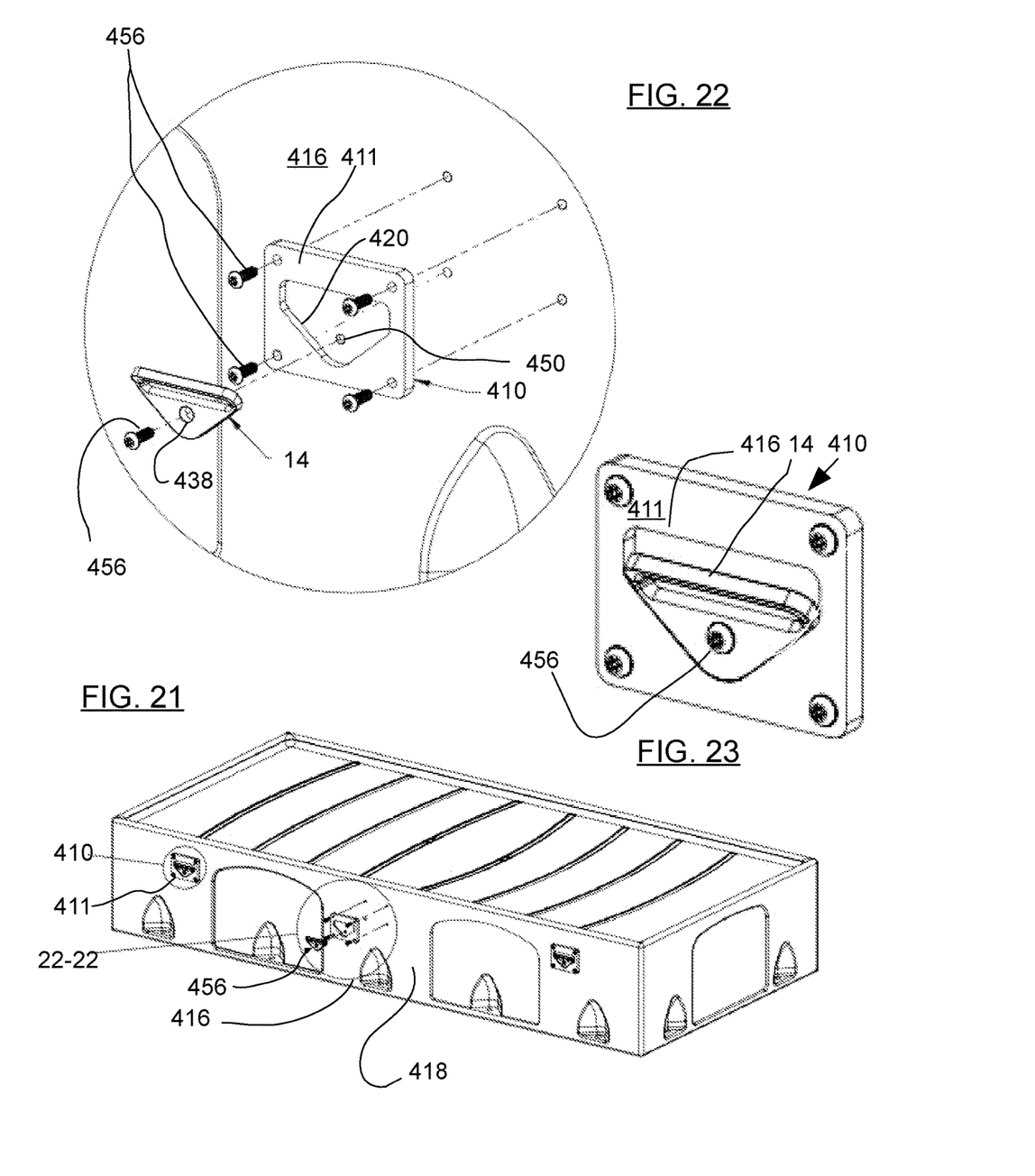
FIG. 21 is an perspective exploded view of a fifth embodiment of the present invention.
FIG. 22 is an exploded section view of the fifth embodiment of the present invention taken at approximately 22-22 of FIG. 21.
FIG. 23 is a section view of the fifth embodiment of the present invention taken at approximately 22-22 of FIG. 21.
Figures 24, 25, 26, 27:
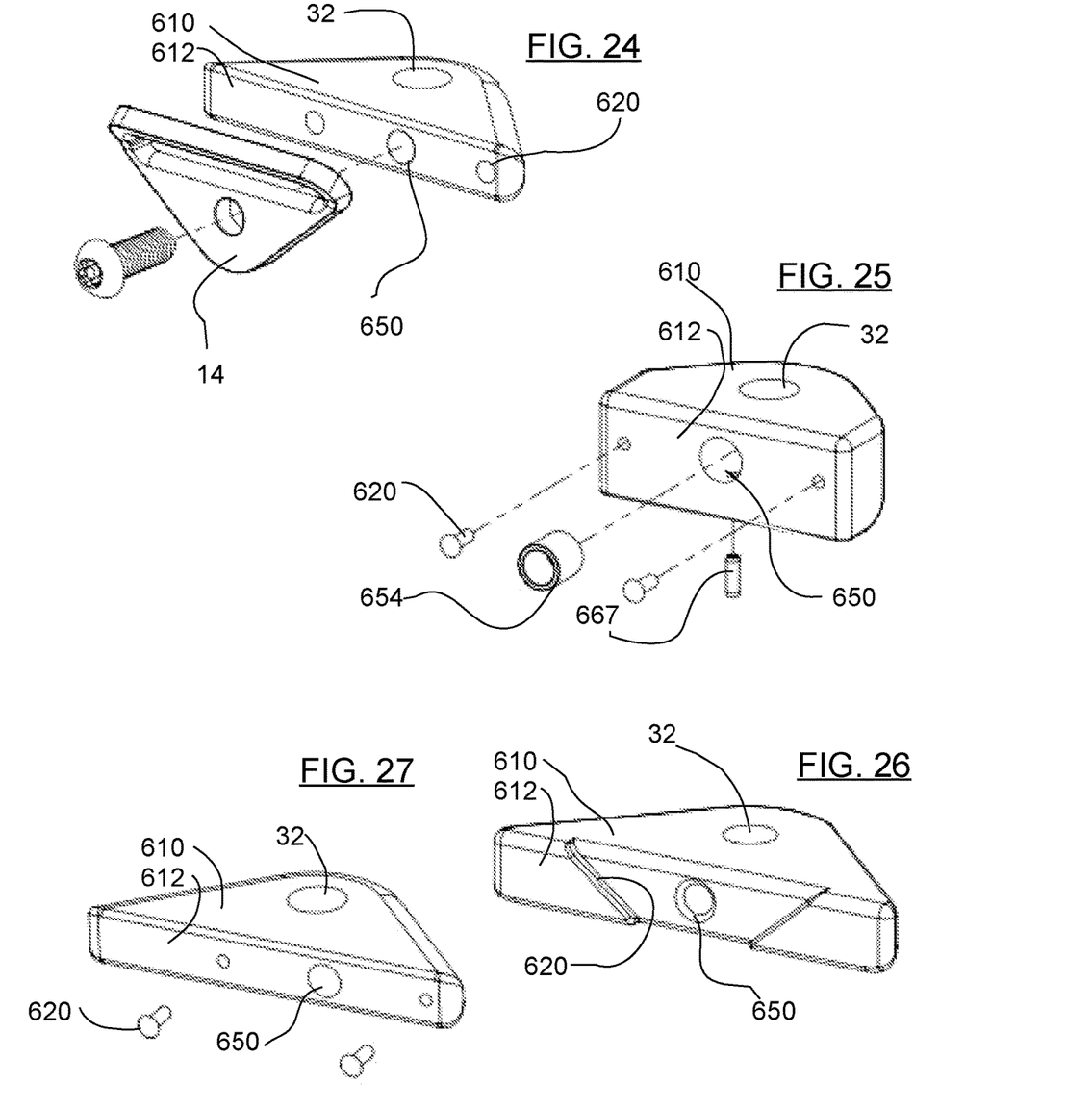
FIG. 24 is an perspective exploded view of the first embodiment of the present invention.
FIG. 25 is an perspective exploded view of a sixth embodiment of the present invention.
FIG. 26 is an perspective exploded view of a seventh embodiment of the present invention.
FIG. 27 is an perspective exploded view of an eight embodiment of the present invention.

Referring to FIGS. 21-23, base 410 may comprise restraint plate 419 attached to bed 416 on bed side wall 418. Base 410 may comprise bolt-on-pocket 411 comprising ring opening 450 and stabilizer edge 420. Restraint ring 14 may fit in pocket 410 having ring opening 450 aligned with restraint hole 438. Tamper resistant quick turn fastener 456 may be adapted to removably attach restraint ring 14 to base 410.

Referring to FIGS. 24-27, base 610 may have different dimensions or have stabilizer 620 formed in front surface 612. Ring opening 650 may have insert 654 attached by pin 667. Ring opening 650 may be centered on front 612. In summary base 10 may be attached to bed 16. base 10 is adapted to releasably connect to restraint ring 14. Quick release fastener 24 extends through restraint ring 14 to releasably attach to base 10. Quick release fastener 24 may be tamper resistant having mechanical, electrical or other quick release lock.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given. Further, the present invention has been shown and described with reference to the foregoing exemplary embodiments. It is to be understood, however, that other forms, details, and embodiments may be made without departing from the spirit and scope of the invention which is defined in the following claims.

We claim:

1. A quick release restraint adapted to attach to a bed, the bed comprising a sidewall, the quick release restraint comprising:
   a restraint ring having a ring base and an open loop portion, the ring base having a restraint hole therein;
   a base, the base secured on the bed sidewall, the base comprising a first base side, a second base side, a mounting surface and a quick release hole, the quick release hole opening onto the mounting surface and extending to the first side, the ring base configured to bear on the mounting surface, the quick release hole configured to be concentrically aligned with the restraint hole; and
   a quick release fastener, the quick release fastener comprising a head, a ring shaft and a retractable locking mechanism, the head configured to bear on the ring base, the ring shaft extending from the head, the ring shaft configured to be inserted in the restraint hole and the quick release hole, the retractable locking mechanism disposed within the ring shaft in a retractable manner, the retractable locking mechanism configured to bear on the base in a locking configuration in which the retractable locking mechanism projects from the ring shaft.

2. The quick release restraint of claim 1, further comprising a stabilizer on the mounting surface, the stabilizer adapted to urge the restraint ring into a predetermined position.

3. The quick release restraint of claim 2, further comprising a base shaft on the ring shaft, the base further comprising a shaft portion, the base shaft configured to be inserted in the shaft portion of the base.

4. The quick release restraint of claim 3, wherein the base further comprises a locking shoulder disposed to bear on the retractable locking mechanism when the retractable locking mechanism is in the locking configuration.

5. The quick release restraint of claim 4, further comprising a release mechanism in the head, the release mechanism configured to actuate the retractable locking mechanism.

6. The quick release restraint of claim 5, wherein the retractable locking mechanism is actuated by a key.

7. The quick release restraint of claim 1, wherein the bed further comprises a fastener cove formed in the sidewall, the fastener cove comprising a side wall and a bottom wall, the first base side configured to bear on the cove side wall.

8. The quick release restraint of claim 1, further comprising a release mechanism in the head, the release mechanism configured to actuate the retractable locking mechanism, the release mechanism adapted to retract the retractable locking mechanism whereby the retractable ball is spaced from locking shoulder of the base.

9. A quick release restraint removably attached to a bed, the bed having a sidewall, the quick release restraint comprising:
   a base on the bed sidewall, the base comprising a mounting surface, a first side, a quick release fastener hole, the quick release fastener hole opening on the mounting surface and extending to the first side, a locking shoulder formed on the base in the quick release fastener hole;
   a restraint ring, the restraint ring having a ring base and a loop portion, a fastener hole in the ring base, the ring base configured to bear on the mounting surface; and
   a quick release fastener, the quick release fastener comprising a head, a shaft and a retractable locking mechanism, the shaft extending from the head, the retractable locking mechanism disposed within the shaft in a retractable manner, the head configured to bear against the ring base, the shaft configured to extending through the fastener hole, the shaft configured to be inserted into the quick release fastener hole, the restraint ring configured to be disposed between the head and the base, the retractable locking mechanism bearing on the locking shoulder in a locking configuration in which the retractable locking mechanism projects from the shaft.

10. The quick release restraint of claim 9 further comprising a release mechanism on the retractable locking mechanism, the release mechanism adapted to actuate the retractable locking mechanism to a non-locking configuration whereby the retractable locking mechanism is spaced from the locking shoulder.

* * * * *